United States Patent
Hwang

(10) Patent No.: US 7,422,736 B2
(45) Date of Patent: Sep. 9, 2008

(54) SOMATIC PLURIPOTENT CELLS

(75) Inventor: Shiaw-Min Hwang, Hsinchu (TW)

(73) Assignee: Food Industry Research and Development Institute (TW)

( * ) Notice: Subject to any disclaimer, the term of this patent is extended or adjusted under 35 U.S.C. 154(b) by 566 days.

(21) Appl. No.: 10/287,362

(22) Filed: Nov. 4, 2002

(65) Prior Publication Data

US 2004/0018617 A1   Jan. 29, 2004

Related U.S. Application Data

(60) Provisional application No. 60/398,883, filed on Jul. 26, 2002.

(51) Int. Cl.
| | |
|---|---|
| A01N 63/00 | (2006.01) |
| A01N 65/00 | (2006.01) |
| C12N 5/00 | (2006.01) |
| C12N 5/02 | (2006.01) |
| C12N 5/10 | (2006.01) |
| C12N 5/08 | (2006.01) |

(52) U.S. Cl. .................. 424/93.1; 424/93.21; 424/93.7; 435/325; 435/363; 435/366; 435/372

(58) Field of Classification Search ................ 424/93.1, 424/93.21, 93.7; 435/325, 363, 366, 372
See application file for complete search history.

(56) References Cited

U.S. PATENT DOCUMENTS

| | | | | |
|---|---|---|---|---|
| 5,453,357 A | * | 9/1995 | Hogan | ........................ 435/7.21 |
| 2001/0024825 A1 | * | 9/2001 | Thomson | ..................... 435/366 |

FOREIGN PATENT DOCUMENTS

| | | |
|---|---|---|
| WO | 01/11001 | 2/2001 |
| WO | 01/21767 | 3/2001 |
| WO | WO 01/21767 | 3/2001 |
| WO | 02/034890 | 5/2002 |
| WO | WO 02/34890 | 5/2002 |
| WO | 02/057430 | 7/2002 |
| WO | 02/064748 | 8/2002 |
| WO | 03/023018 | 3/2003 |
| WO | WO 03/023018 | 3/2003 |

OTHER PUBLICATIONS

Kim et al. 2002, J. of Cell Biol., 159: 821-831.*
Land et al. 1997, J. Appl. Physiol., 82: 776-783.*
Oswald et al., 2004, Stem Cells, 22: 377-284.*
Gage, 1998, Nature, 392: 18-24.*
Thomson et al. 1998, Science, 282: 1145-1147.*
Jiang et al., 2002, Nature, 418:41-49.*
Duran et al., 2001, Int. J. Cancer, 93: 324-332.*
Ostenfeld et al., 2002, Developmental Brain Research, 134, 43-55.*
Wakayama et al., 2001, Science, 292: 740-743.*
Shamblott et al., 1998, PNAS, USA, 95: 13726-13731.*
Donovan and Gearhart, 2001, Nature, 414: 92-97.*
Odorico et al., 2001, Stem Cells: 19: 193-204.*
Sakaguchi et al., 2004, Blood, 104: 2728-2735.*
Goodwin et al. "Multilineage Differentiation Activity by Cells Isolated from Umbilical Cord Blood: Expression of Bone, Fat and Neural Markers". Biology of Blood and Marrow Transplantation 7(11):581-588, 2001.
Pittenger et al. "Multilineage Potential of Adult Human Mesenchymal Stem Cells". Science 284(5411): 143-147, 1999.
Ferrari et al. "Muscle Regeneration by Bone Marrow-Derived Myogenic Progenitors". Science 279:1528-1530, 1998.
Yuehua Jiang, et al. *Pluripotency of mesenchymal stem cells derived from adult marrow*. Nature, 418:41-49, Jul. 2002.
Abuljadeyal, L.S. "Induction of stem cell-like plasticity in mononuclear cells derived from unmobilized adult human peripheral blood". Current Medical Research and Opinions 19(5):355-375, 2003.

* cited by examiner

*Primary Examiner*—Anne Marie Wehbe
*Assistant Examiner*—Joanne Hama
(74) *Attorney, Agent, or Firm*—Occhiuti Rohlicek & Tsao LLP

(57) ABSTRACT

The present invention discloses a cultured somatic animal cell having a normal karyotype; the cell develops into an embryoid body when induced in vitro, or develops into a teratoma when introduced into a SCID mouse. Also disclosed is a method of producing such a cell.

12 Claims, No Drawings

SOMATIC PLURIPOTENT CELLS

RELATED APPLICATION

This application claims priority to U.S. Provisional Application Ser. No. 60/398,883, filed Jul. 26, 2002, the contents of which are incorporated herein by reference.

BACKGROUND

Pluripotent embryonic stem (ES) cells are derived from early mammalian embryos. They can differentiate in vivo into all cell lineages, and, when induced in vitro, differentiate into most cell types. Due to their pluripotency, ES cells are believed to hold a great promise for treating degenerative or inherited diseases. Ethical considerations have hampered the use of human ES cells in research and therapy. Pluripotent cells of a non-embryonic origin (e.g., somatic cells) would circumvent this obstacle.

It has been reported that some somatic cells can develop into cells of unrelated tissue types. However, their developmental potential is limited. There is a need for somatic cells that have unlimited developmental potential.

SUMMARY

In one aspect, the present invention features a cultured somatic animal cell that has a normal karyotype and, when induced in vitro, develops into an embryoid body, i.e., a cellular mass that can further develop into structures having features of an organ. Examples of such structures include a primordial gut, exhibiting regular contraction and relaxation. The cultured cell is somatic since it is of a non-embryonic or non-germ-line origin.

In another aspect, the invention features a cultured somatic animal cell that has a normal karyotype and, when introduced into a severely combined immunodeficient (SCID) mouse, develops into a teratoma. A teratoma is a tumor containing tissues derived from all three embryonic germ layers, i.e., ectoderm, mesoderm, and endoderm. Examples of the tissues include cornea lens and developing epidermis (ectoderm), cartilage and striated muscle (mesoderm), and liver and gastrointestinal tracts (endoderm). In one embodiment, the cultured somatic animal cell, when induced in vitro, can develop into an embryoid body. In anther embodiment, the cultured cell does not express stage-specific embryonic antigen-1 (SSEA-1), i.e., SSEA-1 negative.

In yet another aspect, the invention features a method of producing pluripotent animal cells, such as those described above. The method includes (1) isolating somatic cells from a tissue of an animal; (2) culturing the isolated cells under a starving condition; and (3) identifying and enriching pluripotent cells among the cultured cells. The enriched pluripotent cells, when introduced into SCID mice, develop into teratomas. The somatic cells can be isolated from mammals, including a human. Any suitable tissues can be used to isolate somatic cells for use in this method. Examples of such tissues include umbilical cord blood, bone marrow, amniotic fluid, adipose tissue, placenta, and peripheral blood.

To produce pluripotent cells, the isolated cells are cultured under a starving condition unfavorable for cells to grow, e.g., in a starving medium containing 0.5% to 2% serum for 5-10 days, or in a regular medium containing 10% to 20% serum for 7 to 21 days without changing the medium. A regular medium contains nutrients and factors that promote cell proliferation. A starving medium is low in nutrients and factors for cell proliferation. The nutrients include serum and serum replacements, and the factors include insulin, epidennal growth factors (EGF), acidic fibroblast growth factors (aFGF), and basic fibroblast growth factors (bFGF). Among the cells cultured in a starving condition, pluripotent cells can be identified and enriched based on, for example, their morphology and cell-surface markers (e.g., SSEA-1 negative).

It was unexpected that the pluripotent somatic cells of the invention can be produced under a starving condition. Other features or advantages of the present invention will be apparent from the following detailed description, and also from the claims.

DETAILED DESCRIPTION

The present invention relates to cultured somatic animal cells. These cells are pluripotent since they develop into embryoid bodies when induced in vitro, or develop into teratomas when introduced into SCID mice. The cells have all of the chromosomes, which are characteristic of those in normal cells, and have no noticeable alteration. In other words, they have a normal karyotype.

The cells have phenotypes characteristic of undifferentiated ES cells. In one example, they spontaneously form flattened spheroid colonies in cultures. Similar colonies have been found in the culture of undifferentiated ES cells. See, e.g., Thomson J. et al., Science, 282:1145-1147, 1998. The cells can also show antigenic properties characteristic of undifferentiated ES cells, e.g., not expressing specific stage embryonic antigen (SSEA)-1, but expressing SSEA-3, SSEA-4, TRA-1-60, TRA-1-81, and Oct-4. Oct is a family of transcription factors that are crucial for the development of pluripotent cells. Oct-4, specifically expressed in the mammalian germ line cells and stem cells, is essential for maintaining their pluripotency (see, e.g., Nichols J. et al., Cell, 95:379-391, 1998).

The cells can also have high-level telomerase activity. A telomerase is a ribonucleoprotein that adds telomere repeats to the ends of chromosomes during cell duplication, thereby maintaining lengths of telomeres and chromosomes. High-level expression of telomerase has been found in germ line cells, ES cells, and embryonic tissues, but not in somatic cells. As a result, telomeres (and chromosomes) become shorter in somatic cells after each cell division. Finally, after a finite life span, somatic cells enter senescence due to loss of chromosomal DNA. As restored telomerase expression in somatic cells extends their life span, the high-level telomerase activity in cells of the invention suggests that their life span equals to that of ES cells.

The pluripotent cells of the invention can be produced by isolating somatic cells from a tissue of an animal, culturing the isolated cells under a starving condition, and identifying and enriching the cultured cells. The pluripotent cells can be produced from mesenchynial stem cells isolated from, e.g., umbilical cord blood, bone marrow, amniotic fluid, adipose tissue, placenta, or peripheral blood cells using the method described in Example 2 below or analogous methods well known in the art. See, e.g., Erices A. et al., British J. Haematol., 109:235-242, 2000, Pittenger M. et al., Science, 284:143-147, 1999, Safford K. et al., Biochem. Biophy. Research Comm., 294:371-379, 2002, and Erickson G. et al., Biochem. Biophy. Research Comm., 290:763-769, 2002. The mesenchymal stem cells can be maintained in an alpha-modified MEM containing 10-20% ES-screened fetal bovine serum (FBS) and bFGF, or cultured under a starving condition described above. Neither cell fusion nor nucleus transferring is required in converting the mesenchymal stem cells to pluripotent cells under the starving condition. After the starving process, pluripotent somatic cells can be identified according to their morphology (e.g., cell size and shape), enzymatic activity (e.g., alkaline phosphatase and telomerase), and surface makers (e.g., SSEA-1 negative, SSEA-3 positive, and SSEA-4 positive). The identified cells can be enriched using any suitable cell separation techniques known in the art. For example, as cells tend to form colonies, one can directly pick up the colonies using a micropipette under a microscope. To more rapidly enrich a large amount of cells, one can use the fluorescence-activated cell sorting (FACS) techniques. For example, anti-SSEA-3 monoclonal antibodies, anti-SSEA-4 monoclonal antibodies, and anti-SSEA-1 monoclonal antibodies linked with different fluorescent labels are used to enrich cells that are SSEA-3 positive, SSEA-4 positive, and SSEA-1 negative. These cells can be further examined for their pluripotency.

One can test the pluripotency of the cells using any suitable methods. For example, one uses the in vivo teratoma-forming assay as described in Example 5 below. As a teratoma contains the derivatives of all three embryonic germ layers, the capacity of a cell to form a teratoma indicates that the cell is pluripotent. Alternatively, one can use the in vitro embryoid body-forming assay as described in Example 6 below. Formation of an embryoid body indicates that the cell is pluripotent.

The cells of the invention can be used in a variety of ways. One can use the cells for treating degenerative or inherited diseases, avoiding ethical considerations of human embryo manipulation. To do so, one can isolate mesenchymal stem cells from a patient, e.g., lacking a functional gene essential for proper development of a tissue or organ. After producing pluripotent cells, he or she can introduce into the cells an expression nucleic acid vector encoding a functional version of the gene. The vector can be introduced into the cells via a variety of techniques, including calcium phosphate co-precipitation, DEAE-dextran-mediated transfection, lipofection, electroporation, microinjection, or virus-meditated techniques. Methods not affecting the pluripotency of the cells are preferred. Description of such techniques can be found in, e.g., U.S. Pat. No. 5,591,625 and U.S. Patent Application No. 20020127715. After delivering the functional gene into the cells, one can transplant the cells back into the patient using method known in the art. As the cells are produced from the patient, the treatment does not cause immune rejection. Under proper conditions, the transplanted cells can develop into a functional tissue or organ. To facilitate this development, the patient may be administered with factors to induce the development of the cells. Such factors can be small molecule compounds, peptides, and nucleic acids. Examples include, but are not limited to, transforming growth factor β, bone morphogenic proteins, and nerve growth factor.

The cells of the invention are also useful for studying development/differentiation mechanisms of embryos. One can identify conditions for inducing the development of pluripotent cells into a specific tissue or organ using such cells as a model system. Further, one can isolate genes that play roles during the development of embryos using differential cDNA screening as described in, e.g., Shen M. et al., Development, 124:429-42, 1997. One can prepare a cDNA library from the pluripotent cells that have been induced to develop, e.g., into the embryoid bodies described above. The library is plated on two sets of replica filters. One set of filters (set A) is screened with cDNA made from uninduced cells. The other set of filters (set B) is screened with a comparable amount of cDNA made from induced cells. The cDNA used for screening the library can be labeled and visualized using methods well known in the art. One can then select, from the library, cDNA clones displaying stronger hybridization signals on set B than on set A. These cDNAs encodes gene that are over-expressed in the induced cells. Vice versa, genes over-expressed in the uninduced pluripotent cells can be isolated. By the same token, one can also isolate genes over-expressed in cells before and after the above-described starving process. All of these isolated genes can be further studied to define their roles in respective processes.

The pluripotent cells produced from non-human animals can be used to develop into organs or clones of the animals using the methods as described in, e.g., Campbell K. et al., Nature, 380: 64-66, 1996. Accordingly, these cells are valuable for the pet and livestock industries, and can be used to preserve endangered animals.

A number of embodiments of the invention have been described. Nevertheless, it will be understood that various modifications may be made without departing from the spirit and scope of the invention. Accordingly, other embodiments are within the scope of the following claims.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Immunocytochemistry staining was performed to examine cell markers.

For staining cell-surface markers, cells were fixed with 4% paraformaldehyde at 20° C. for 10 minutes. For staining of cytoskeletal proteins, cells were fixed with methanol at −20° C. for 2 minutes and permeabilized with 0.1% Triton X-100 for 10 minutes. For staining other intracellular molecules, cells were fixed with 4% paraformaldehyde at 20° C. for 10 minutes and permeabilized with 0.1% Triton X-100 for 10 minutes.

The fixed cells were incubated for 30 minutes in a blocking solution containing phosphate-buffered saline (PBS), 1% bovine serum albumin (BSA), and 1% serum (Sigma, St. Louis, Mo.) from species same to the species in which the primary antibody was raised. The cells were then incubated sequentially for 60 minutes each with primary antibodies properly diluted in the blocking solution, biotinylated anti-mouse secondary antibody, and strepavidin-conjugated horseradish peroxidase. Between each step, cells were washed with PBS containing 0.3% BSA for 10 minutes. The horseradish peroxidase activity was visualized by incubating with diaminobenzidine chromagen (Vector Laboratories Inc., CA). After the visualization, the cells were examined under a microscope, and pictures were taken.

EXAMPLE 2

Mesenchymal stem cells were isolated from bone marrow and umbilical cord blood.

Human bone marrow was purchased from BioWhittaker, Inc. (Walkersville, Md.). Umbilical cord blood was obtained from subjects with noticed consent. To isolate mesenchymal stem cells, mononuclear cells were prepared from the human bone marrow or umbilical cord blood using Ficol-paque (d=1.077 g/ml, Amersham Biosciences, Piscataway, N.J.) density gradient method as described in, e.g., Erices A. et al., British J. Haematol., 109:235-242, 2000 or Pittenger M. et al., Science, 284:143-147, 1999.

Isolated mononuclear cells were seeded at a concentration of 1×10⁶ cells/cm² in tissue culture dishes containing a regular medium, an alpha-modified minimum essential medium (MEM) with 20% ES cell-screened FBS (Hyclone, Logan, Utah), 4 ng/ml b-FGF, 100 U/ml penicillin and 100 ug/ml streptomycin (Invitrogen, Carlsbad, Calif.). After two weeks of culturing, many cells adhered to the culture dishes. These morphologically homogenous cells were self-renewing with a doubling time of 32-36 hours.

The adherent cells were further characterized using immunocytochemistry staining as described above. Antibodies against CD34 or CD45 (cell surface antigens of heamatopoeitic lineage) were purchased from Bacton Dickinson (Mountain View, Calif.). The staining results revealed the cells were negative for CD34 and CD45, suggesting that the cells did not belong to heamatopoeitic lineage. Further, the cells could be induced to differentiated into osteocytes, chondrocytes and adipocytes using appropriate media according the methods described in, e.g., Pittenger M. et al., Science, 284:143-147, 1999. Differentiated osteocytes were analyzed using von Kossa staining method. Differentiated chondocytes were stained by Safranin O. Adipocytes were stained by Oil Red O. The above methods can be found in e.g., Colter D. et al., Proc. Natl. Acad. Sci. USA. 98: 7841-7845, 2001. These results indicated that the isolated cells were the mesenchymal stem cells (Prockop D. et al., Nature, 276:71-74, 1997.). Nonetheless, the developmental potential of these cells is limited since they could not develop into teratomas when introduced in SCID mice or into embryoid bodies when induced. See Examples 5 and 6 below.

EXAMPLE 3

The isolated mesenchymal stem cells described above were cultured under a starving condition to generate pluripotent cells.

The mesenchymal stem cells were cultured in the regular medium described in Example 2 for three to five passages. The cells were then placed in an alpha-modified MEM containing 0.5% FBS in the absence of b-FGF (a starving medium) for 5-7 days. Alternatively, the cells were maintained in the regular medium without changing the medium for two weeks. During the above starvation processes, the cells were monitored under a microscope daily, and no cell fusion was found. At the end of the starvation process, round and flattened colonies appeared in the cultures. Each of the colonies was picked using a micropipette and maintained in an undifferentiated state on mouse feeder cells, e.g., mitomycin-treated mouse STO cells (ATCC CRL-1503) or mouse embryonic fibroblast cells, in an Iscove's modified Dulbecco's medium (IMDM) with 20% ES-screened FBS, 4 ng/ml bFGF, and 0.1 mM 2-mercaptoethanol. Cells from each colony could be maintained in the undifferentiated state and continue to proliferate for over four months (or more than 15 passages).

EXAMPLE 4

Morphology, cell marker expression, enzymatic activity, and karyotypes of the cells from the colonies were examined.

The cells were examined under a light microscope or a scanning electron microscope. For a scanning electron microscopic examination, the cells were cultured on a Melinex film (DuPont, Hopewell, Va.), fixed in 2% Osmium tetroxide (w/v), 0.1M phosphate buffer pH 7.4 for 16 hours at 4° C. and dehydrated through a graded ethanol series. After critical-point drying using liquid carbon dioxide and sputter coating with chromium, the cells were examined under the field emission of a scanning electron microscope (SEM) Leo 982 (LEO Elektronenmilkroskopie GmbH, Germany) operated at 2 kV. See, e.g., Bozzola J. et al., 1992. Specimen preparation for scanning electron microscopy. In: Electron Microscopy: Principles and Techniques for Biologists. pp. 40-62. Jones and Bartlett Publishers, Boston. As the microscopic photographs indicated, the morphology of the cells was similar to that of undifferentiated ES cells, such as those described in Thomson J. et al., Science, 282:1145-1147, 1998.

The cells were also characterized using immunocytochemistry staining as described above. Antibodies against SSEA-1 (MC-480, 1:50), SSEA-3 (MC-631, 1:50) and SSEA-4 (MC-813-70, 1:50) were obtained from Developmental Studies Hybridoma Bank, University o Iowa (Iowa city, Iowa). Anti-TRA-1-60 and anti-TRA-1-81 antibodies were obtained from Santa Cruz Biotechnology, Inc. (Santa Cruz, Calif.). The results indicated that the cells were negative for SSEA-1 and positive for SSEA-3, SSEA-4, TRA-1-60, and TRA-1-81. The expression of transcription factor Oct-4 was also detected by reverse transcription-PCR as described in Reubinoff B. et al., Nature Biotechnol., 18:399-404, 2000.

The alkaline phosphatase activity of the cells was detected using a Sigma 86-R kit following the manufacture's instruction (Sigma, St. Louis, Mo.). The cells exhibited high level alkaline phosphatase activity. The cells were also examined for their telomerase activity using the TRAPeze ELSIA telomerase detection as described in Kim N. et al., Science, 266:2011-2015, 1994. The results revealed a high-level telomerase activity in the cells.

Karyotypes of the cells were determined using the method described in e.g., ISCN 1995: An International System for Human Cytogenetic Nomenclature (F. Mitelman, ed.) Karger, Basel (1995). Briefly, the cells were subcultured at a 1:4 dilution 12 hours before harvesting. The cells were collected with trypsin-EDTA and incubated with colcemid for 1.5 hours followed by lysis with hypotonic KCl and fixation in acid/alcohol. Metaphases were analyzed using methods as described by, e.g., Freshney, R in "Culture of animal cells—A manual of basic technique" 3ʳᵈ edition. A John Wiley & Sons, Inc. New York (1994), pp 205-209. The result revealed that the cells had all 46 chromosomes of human. The chromosomes had no noticeable alteration as compared to normal human chromosomes.

EXAMPLE 5

To test the pluripotency of the cells prepared as described in Example 3, the teratoma-forming assay was carried out.

Approximately 1×10⁵ cells were implanted into the hind leg musculature of SCID mice. Teratomas were observed 6-8 weeks after injection. The teratomas were harvested and subjected to histological examination using the method as described Thomson J. et al., Science, 282:1145-1147, 1998. All tumors examined contained tissues derived from all three embryonic genn layers: developing gastrointestinal tract (endoderm); cartilage, bone, and striated muscle (mesoderm); and cornea lens, fragmented keratin and developing epidermis (ectoderm). As a control, the mesenchymal stem cells described in Example 2 did not develop into teratomas in SCID mice.

EXAMPLE 6

The embryoid body-forming assay was performed to test the pluripotency of the cells prepared Example 3.

The cells were cultured in non-coated bacteriologic Petri dishes for 4-6 days. The cells multiplied and formed spheroids (embryoid bodies) in suspension. The embryoid bodies were transferred and seeded onto chamber-slides coated with 0.1% gelatin. After one week in culture, multiple clusters emerged from outgrowth of the spheroids. Each of the clusters displayed regular contraction and relaxation at 5-7 seconds per cycle for more than 12 hours. This mechanical activity was similar to that of a gut-like organ (primordial gut) developed from ES cells as described in Yamada T. et al., Stem Cells, 20:41-49, 2002. In contrast, the mesenchymal stem cells could not develop into embryoid bodies when they were induced under the same condition.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of producing pluripotent human cells, the method comprising:
   isolating mesenchymal stem cells from a tissue of a human;
   culturing the isolated cells under a starving condition, wherein the culturing step is performed by placing cells in a medium containing 0.5% to 2% serum for 5 to 10 days or in a medium containing 10% to 20% serum for 7 to 21 days without changing the medium; and
   identifying and enriching pluripotent cells among the cultured cells,
   wherein the pluripotent cells, when introduced in a SCID mouse, develop into a teratoma.

2. The method of claim 1, wherein the pluripotent cells are stage-specific embryonic antigen-1 negative.

3. The method of claim 1, wherein the tissue is umbilical cord blood, bone marrow, amniotic fluid, adipose tissue, placenta, or peripheral blood.

4. The method of claim 3, wherein the pluripotent cells are stage-specific embryonic antigen-1 negative.

5. The method of claim 3, wherein the tissue is umbilical cord blood, bone marrow, or amniotic fluid.

6. The method of claim 5, wherein the pluripotent cells are stage-specific embryonic antigen-1 negative.

7. The method of claim 5, wherein the culturing step is performed by placing cells in a medium containing 0.5% serum for 5-7 days or in a medium containing 20% serum for 2 weeks without changing the medium.

8. The method of claim 7, wherein the pluripotent cells are stage-specific embryonic antigen-1 negative.

9. The method of claim 3, wherein the culturing step is performed by placing cells in a medium containing 0.5% serum for 5-7 days or in a medium containing 20% serum for 2 weeks without changing the medium.

10. The method of claim 9, wherein the pluripotent cells are stage-specific embryonic antigen-1 negative.

11. The method of claim 1, wherein the culturing step is performed by placing cells in a medium containing 0.5% serum for 5-7 days or in a medium containing 20% serum for 2 weeks without changing the medium.

12. The method of claim 11, wherein the pluripotent cells are stage-specific embryonic antigen-1 negative.

* * * * *